United States Patent
Franke et al.

(10) Patent No.: US 11,185,628 B2
(45) Date of Patent: Nov. 30, 2021

(54) MEDICAMENT DELIVERY SYSTEM

(71) Applicant: SANOFI, Paris (FR)

(72) Inventors: Beate Franke, Frankfurt am Main (DE); Bernhard Forys, Frankfurt am Main (DE); Stefan Verlaak, Paderno d'Adda (IT); Ilario Melzi, Milan (IT)

(73) Assignee: Sanofi, Paris (FR)

(*) Notice: Subject to any disclaimer, the term of this patent is extended or adjusted under 35 U.S.C. 154(b) by 260 days.

(21) Appl. No.: 16/317,618

(22) PCT Filed: Jul. 12, 2017

(86) PCT No.: PCT/EP2017/067513
§ 371 (c)(1),
(2) Date: Jan. 14, 2019

(87) PCT Pub. No.: WO2018/011258
PCT Pub. Date: Jan. 18, 2018

(65) Prior Publication Data
US 2019/0282752 A1 Sep. 19, 2019

(30) Foreign Application Priority Data
Jul. 14, 2016 (EP) .................................. 16305916

(51) Int. Cl.
*A61M 5/14* (2006.01)
*A61M 5/142* (2006.01)
(Continued)

(52) U.S. Cl.
CPC ...... *A61M 5/14248* (2013.01); *A61M 5/3287* (2013.01); *A61M 2005/14252* (2013.01); *A61M 2005/14506* (2013.01)

(58) Field of Classification Search
CPC .............. A61M 5/142; A61M 5/14244; A61M 5/14248; A61M 5/14276; A61M 5/145;
(Continued)

(56) References Cited

U.S. PATENT DOCUMENTS

| 5,911,716 A | 6/1999 | Rake et al. |
| 6,358,239 B1 * | 3/2002 | Rake ..................... A61M 5/148 |
| | | 128/DIG. 12 |

(Continued)

FOREIGN PATENT DOCUMENTS

| CN | 2429179 | 5/2001 |
| CN | 102753225 | 10/2012 |

(Continued)

OTHER PUBLICATIONS

International Preliminary Report on Patentability in Application No. PCT/EP2017/067513, dated Jan. 15, 2019, 10 pages.
(Continued)

*Primary Examiner* — William R Carpenter
(74) *Attorney, Agent, or Firm* — Fish & Richardson P.C.

(57) ABSTRACT

A medicament delivery system for use with medicament delivery device includes a support member, a compression member spaced from the support member to define a gap therebetween, a mechanical coupling between the support member and the compression member comprising a plurality of connecting members extending between the support member and the compression member, and a biasing element connected to the compression member and configured to exert a rotational force on the compression member relative to the support member. The mechanical coupling is configured such that rotation of the compression member relative to the support member causes the compression member to be drawn towards the support member to reduce the gap therebetween.

26 Claims, 7 Drawing Sheets

(51) Int. Cl.
*A61M 5/32* (2006.01)
*A61M 5/145* (2006.01)

(58) Field of Classification Search
CPC ...... A61M 2005/14506; A61M 5/1452; A61M 5/1454; A61M 5/14586
See application file for complete search history.

(56) References Cited

U.S. PATENT DOCUMENTS

| | | |
|---|---|---|
| 6,669,668 B1 | 12/2003 | Kleeman et al. |
| 2005/0238512 A1* | 10/2005 | Luharuka ............ F04B 19/006 417/437 |
| 2007/0066935 A1* | 3/2007 | Morishita .......... A61K 38/1833 604/68 |
| 2010/0130931 A1* | 5/2010 | Yodfat ................ A61M 5/172 604/151 |
| 2012/0109066 A1 | 5/2012 | Chase et al. |
| 2014/0228759 A1 | 8/2014 | Soma et al. |

FOREIGN PATENT DOCUMENTS

| | | |
|---|---|---|
| JP | H05-220204 | 8/1993 |
| JP | H07-503162 | 4/1995 |
| JP | 2013-070716 | 4/2013 |
| WO | WO 1993/014797 | 8/1993 |
| WO | WO 2006/008465 | 1/2006 |
| WO | WO 2009/085407 | 7/2009 |
| WO | WO 2011/075104 | 6/2011 |
| WO | WO 2015/063562 | 5/2015 |

OTHER PUBLICATIONS

International Search Report and Written Opinion in Application No. PCT/EP2017/067513, dated Sep. 25, 2017, 14 pages.

* cited by examiner

MEDICAMENT DELIVERY SYSTEM

CROSS REFERENCE TO RELATED APPLICATIONS

The present application is the national stage entry of International Patent Application No. PCT/EP2017/067513, filed on Jul. 12, 2017, and claims priority to Application No. EP 16305916.5, filed on Jul. 14, 2016, the disclosures of which are incorporated herein by reference.

TECHNICAL FIELD

The present invention relates to a system for delivery of a liquid medicament, particularly for use with medical injector devices.

BACKGROUND

A variety of diseases exist that require regular treatment by injection of a medicament. Injection devices known in the art include infusion and patch pumps for delivering injections of medicament. Another type of injection device is a bolus injector device. Some biological medicaments comprise higher viscosity injectable liquids and are to be administered in larger volumes than traditional liquid medicaments, typically at least 1 ml and maybe a few ml. Such high capacity bolus injectors can be called large volume devices (LVDs). Such injection devices may be first supported on a suitable injection site of a patient and, once installed, injection is initiated by the patient or another person (a user).

The drug delivery process of such devices can last for several minutes or even hours, particularly in the case of large volume devices. However, for effective treatment of the medical condition, it is important that the device reliably and completely delivers the entire medicament dose to the patient.

SUMMARY

In certain aspects, a medicament delivery system for use with a medicament delivery device is provided, the medicament delivery system comprising a support member, a compression member spaced from the support member to define a gap therebetween, a mechanical coupling between the support member and the compression member comprising a plurality of connecting members extending between the support member and the compression member, and a biasing element connected to the compression member and configured to exert a rotational force on the compression member relative to the support member, wherein the mechanical coupling is configured such that rotation of the compression member relative to the support member causes the compression member to be drawn towards the support member to reduce the gap therebetween.

Each connecting member may be pivotally connected to the support member and to the compression member.

Each connecting member may be pivotally connected to the support member and the compression member by a ball and socket coupling. This may advantageously facilitate rotational movement of the compression member relative to the support member.

The connecting members may comprise inextensible rigid rods. This may advantageously facilitate constant translation of the compression member relative to the support member upon rotation of the compression member.

The biasing element may also be configured to bias the compression member towards the support member. This may advantageously facilitate compression of a body between the support and compression members.

The biasing member may comprise a spiral torsion spring. This may advantageously facilitate rotational biasing of the compression member.

The spiral torsion spring may be conically shaped. This may advantageously facilitate compact and/or space-efficient packaging of the biasing member, such as within a medicament delivery device.

The support member and the compression member may comprise substantially parallel spaced plates. This may advantageously facilitate retention of a body between the plates.

The medicament delivery system may further comprise a collapsible medicament reservoir disposed in the gap between the support member and the compression member. This may advantageously facilitate containment and delivery of a medicament.

In certain aspects, a medicament delivery device comprising a housing, a medicament delivery system as described above disposed within the housing, and an injection needle fluidly connected to the medicament reservoir is provided.

The medicament delivery device may include a releasable locking mechanism configured to retain the compression member against the biasing force of biasing element. This may advantageously facilitate holding the compression member apart from the support member until a medicament delivery process is to be initiated.

The locking mechanism may include an actuator operable to release compression member to move from an expanded state to a compressed state under the biasing force of the biasing element. This may advantageously facilitate initiation of a medicament delivery process.

The medicament delivery device may further comprise a needle control mechanism configured to move the needle between a retracted position in which it is disposed within the housing, and an extended position in which it projects from the housing. This may advantageously facilitate prevention of needle exposure until a medicament delivery process is to be initiated.

The medicament reservoir may contain liquid medicament.

In certain aspects, a method of operating a medicament delivery system for use with a medicament delivery device is provided, the medicament delivery system comprising a support member, a compression member spaced from the support member to define a gap therebetween, a collapsible medicament reservoir disposed within said gap, a mechanical coupling between the support member and the compression member comprising a plurality of connecting members extending between the support member and the compression member, and a biasing element connected to the compression member, the method comprising the biasing member exerting a rotational force on the compression member relative to the support member, the mechanical coupling converting rotation of the compression member relative to the support member to move the compression member towards the support member to reduce the gap therebetween and collapsing the medicament reservoir to expel liquid medicament from the medicament reservoir.

BRIEF DESCRIPTION OF THE FIGURES

Embodiments of the invention will now be described, by way of example only, with reference to the accompanying drawings, in which.

DETAILED DESCRIPTION

A fluid medicament delivery device 1 for delivering fluid medicament to a patient is described below. The device 1 as shown comprises a medicament injection device, although other types of medicament delivery devices are intended within the scope of certain aspects of the invention. The device 1 comprises a medicament delivery system 2 for delivering liquid medicament to the patient. The delivery system 2 may comprise a medicament reservoir 3 for storing a quantity of medicament. The device 1 is configured to be worn against a patient's skin and to deliver the medicament by injection. The device 1 is described below in the context of a bolus injector, but it will be appreciated that it could alternatively be another type of Large Volume Device (LVD) or other medicament injection device.

Figure 1:
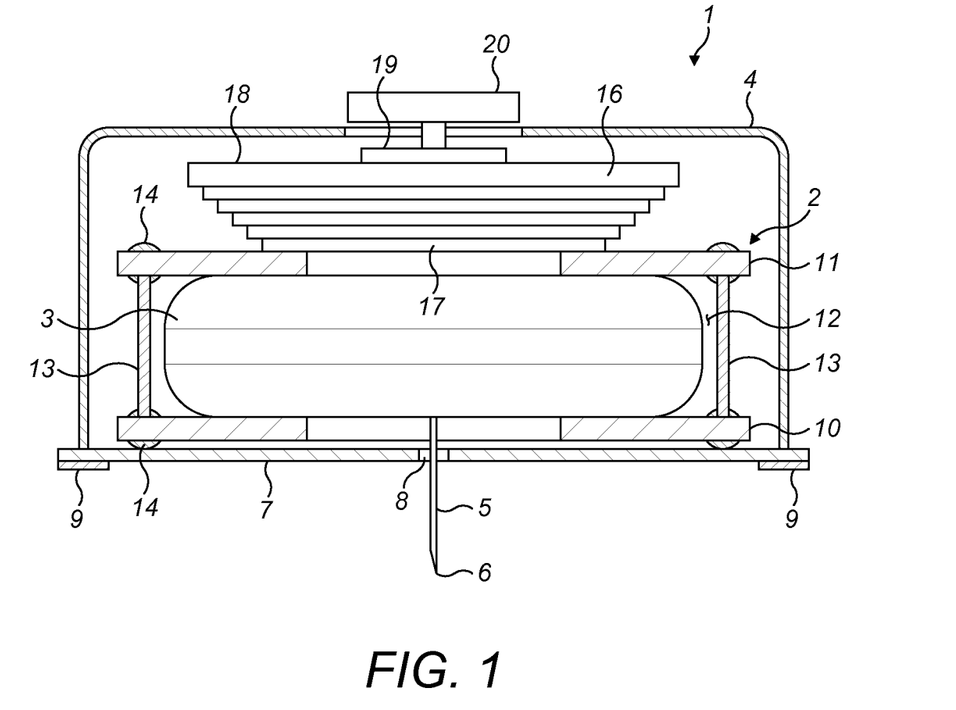
FIG. 1 shows a schematic sectional view of a medicament injection device of an embodiment, including a medicament delivery system of an embodiment.
Figure 2:
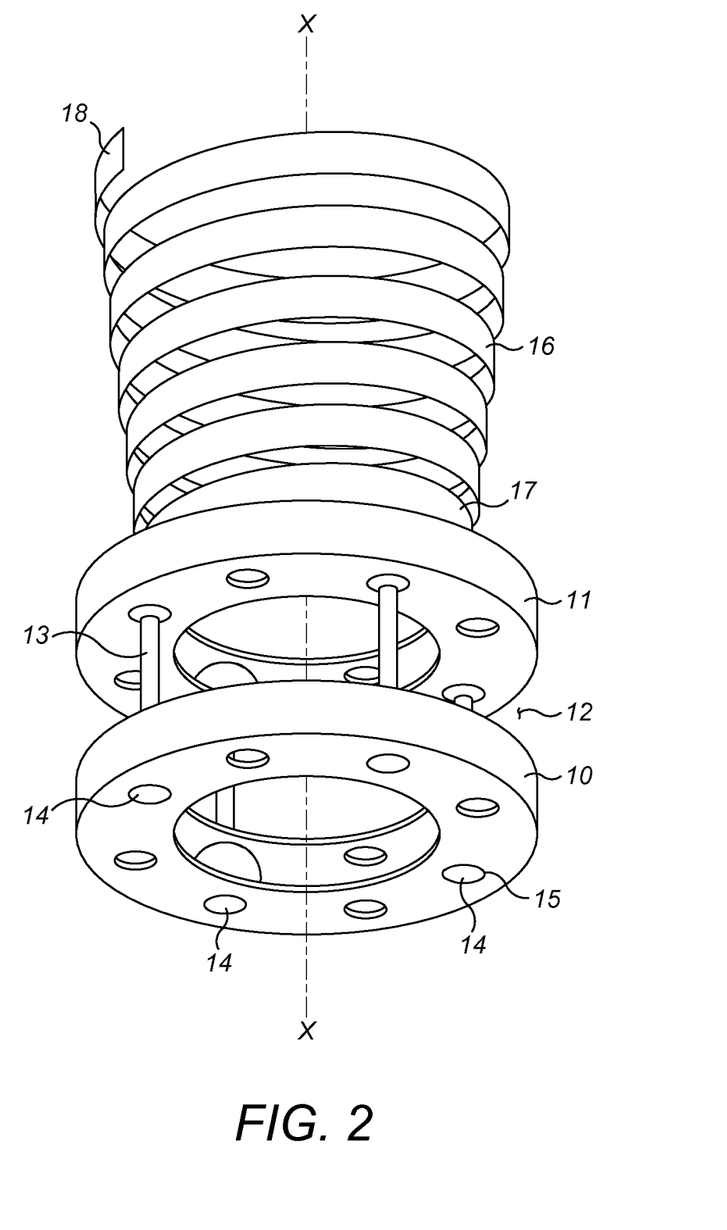
FIG. 2 shows a perspective view of the medicament delivery system of FIG. 1 in an expanded state, without a medicament container.

Referring to FIG. 1, the device 1 comprises a housing 4 in which the delivery system 2, including the medicament reservoir 3 is located, together with other components of the device 1 (not all shown). The housing 4 is formed from moulded plastics or another suitable material. The medicament reservoir 3 is provided as a flexible and/or collapsible container 3, which may contain a single dose of the medicament. The medicament reservoir 3 may be replaceable to allow re-use of the device 1. Alternatively, the medicament reservoir 3 may be non-replaceable in the device 1 so that, once the medicament within the medicament reservoir 3 has been expelled, the device 1 can no longer be used to deliver medicament and must be disposed of. This single-use nature of the device 1 facilitates ease of operation and improves safety by ensuring that a patient cannot mistakenly install an incorrect replacement medicament reservoir 3.

The device 1 includes an injection element for injection of the medicament from the device 1 into the patient. The injection element is explained below in the context of a hollow injection needle 5, as illustrated in FIG. 1. However, other injection elements are envisaged within the scope of certain aspects of the invention, as discussed below, although it will be appreciated that other types of injection element could alternatively be used. The medicament is delivered through the needle 5. A proximal end (not shown) of the needle 5 is fluidly connected to the medicament reservoir 3. The needle 5 is therefore arranged to receive medicament from the medicament reservoir 3. The needle 5 comprises a distal end 6 which, during use, protrudes through the housing 4 of the device 1 into the body tissue of the patient.

Figure 7:
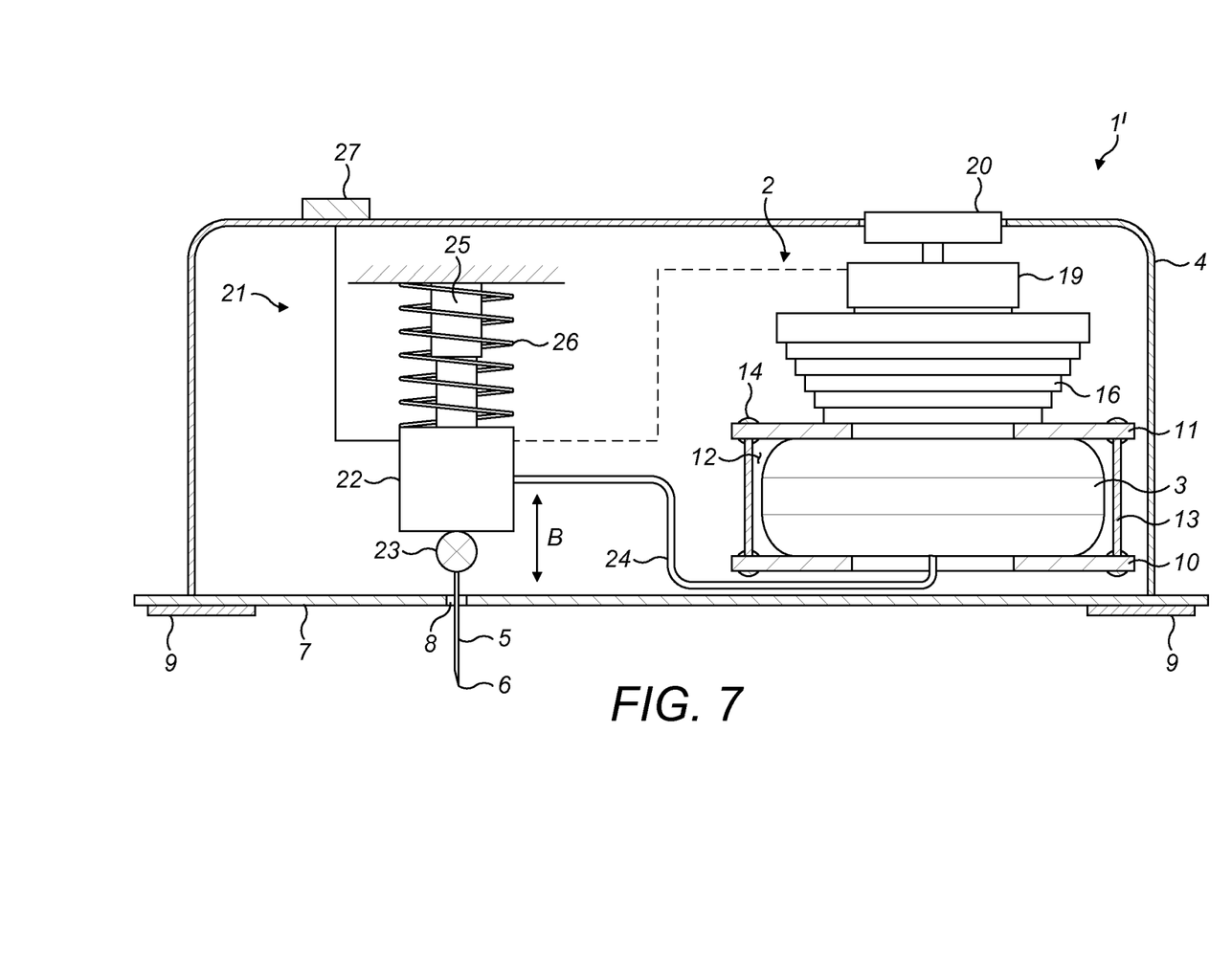
FIG. 7 shows a schematic sectional view of a medicament injection device of another embodiment, including a medicament delivery system of an embodiment.

The injection needle 5 may be controllably extendable and/or retractable through the exterior of the housing 4 in order to allow it to be safely stowed in the housing 4 when not in use. Such a control mechanism is not shown in FIG. 1, although is described with reference to FIG. 7 showing an alternative embodiment, hereafter. Such control mechanism may also include means to control delivery of the medicament from the medicament reservoir 3 through the needle 5 and/or may automatically extend and retract the needle 5 during a medicament delivery program.

The housing 4 includes a contact region 7 arranged to be worn against the skin of the patient during use of the device 1. The contact region 7 comprises a contact face of the housing 4 in the exemplary embodiment shown in FIG. 1. The contact region 7 may have geometric and tactile properties that are selected to be comfortable when worn against the skin of the patient. The contact region 7 includes an aperture 8 through which the injection needle 5 protrudes into the body tissue of the patient during delivery of the medicament.

During use of the device 1, the contact region 7 is held against the skin of the patient by a fastener. The fastener is suitable for holding the contact region 7 in a stable position against the skin for a significant period of time, such as several hours, in order to ensure that the injection needle 5 is maintained in a fixed position relative to the body of the patient during use of the device 1. The exemplary fastener shown in FIG. 1 is an adhesive layer 9 for temporarily adhering the contact region 7 to the skin of the patient. The adhesive layer 9 may comprise a standard biocompatible glue, as used in common adhesive bandages. In order to protect the adhesive layer 9 from damage and to prevent it from sticking to unwanted objects prior to it being attached to the skin of the patient, the contact region 7 of the device 1 may include a protective covering (not shown) which overlies the adhesive layer 9. The protective covering is selectively removable from the contact region 7 in order to expose the adhesive layer 9 before use of the device 1, for example by peeling the covering away from the adhesive layer 9.

The medicament delivery system 2 of the medicament injection device 1 comprises a support member in the form of a support plate 10 and a compression member in the form of a compression plate 11. The support plate 10 and compression plate 11 are substantially parallel to, and spaced from each other. The support and compression members 10, 11 are preferably substantially rigid planar components. In the embodiment shown, the support and compression plates 10, 11 are circular and coaxial about a common axis X-X. A gap 12 is defined between the support plate 10 and the compression plate 11. The medicament reservoir 3 is disposed in the gap 12 and is contacted on opposite sides by the support plate 10 and the compression plate 11. The support member 10 is fixed relative to the housing 4. The compression member 11 is moveable relative to the support member 10 and to the housing 4.

A mechanical coupling connects the support plate 10 and compression plate 11 in a manner that permits the compression plate 11 to rotate relative to the support plate 10 about the axis X-X, and also permits the compression plate 11 to move towards and away from the support plate 10 in the axial direction. Furthermore, the mechanical coupling is configured such that rotation of the compression plate 11 relative to the support plate 10 causes the compression plate 11 to move towards and away from the support plate 10. The mechanical coupling comprises a plurality of connecting members in the form of rigid connecting rods 13. Each connecting rod 13 is connected at one end to the support plate 10 and at its other end to the compression plate 11. In the embodiment shown, the connections between the connecting rods 13 and the support plate 10/compression plate 11 comprise ball-and-socket type joints. Each connecting rod 13 has a ball element 14 at each end. The support plate 10 and compression plate 11 are each formed with part-spherical sockets 15 configured to receive and rotatably retain the ball elements 14 of the connecting rods 13.

A biasing member is provided on the opposite side of the compression member 11 to the medicament reservoir 3. The biasing member is configured to at least exert a rotational force on the compression member 11 to urge the compression member 11 to rotate relative to the support member 10. In the exemplary embodiment shown, the biasing member is in the form of a conical torsion spring 16. A first end 17 of the torsion spring 16 is secured to the compression plate 11. A second, opposite end 18 of the torsion spring 16 is fixedly secured relative to the housing 4. The second end 18 may be fixedly secured to the housing 4 itself, or to a component or mechanism that is fixed relative to the housing 4. The conical torsion spring 16 may also be configured to exert a force on the compression plate 11 to bias the compression plate 11 towards the support plate 10, substantially in a direction of axis X-X.

The device 1 includes a locking mechanism 19 configured to engage with the compression plate 11 and/or the torsion spring 16 to hold the support plate 10 in place against the force of the torsion spring 16. The locking mechanism 19 may be provided in the housing 4 and the second end 18 of the torsion spring 16 may be secured to the locking mechanism 19. The locking mechanism 19 includes a release button 20 accessible from the outside of the housing 4. The release button 20 may be operable by a user to disengage the locking mechanism 19 to release the compression plate 11/torsion spring 16 to allow the compression plate 11 to move under the biasing force of the torsion spring 16.

Figure 3:
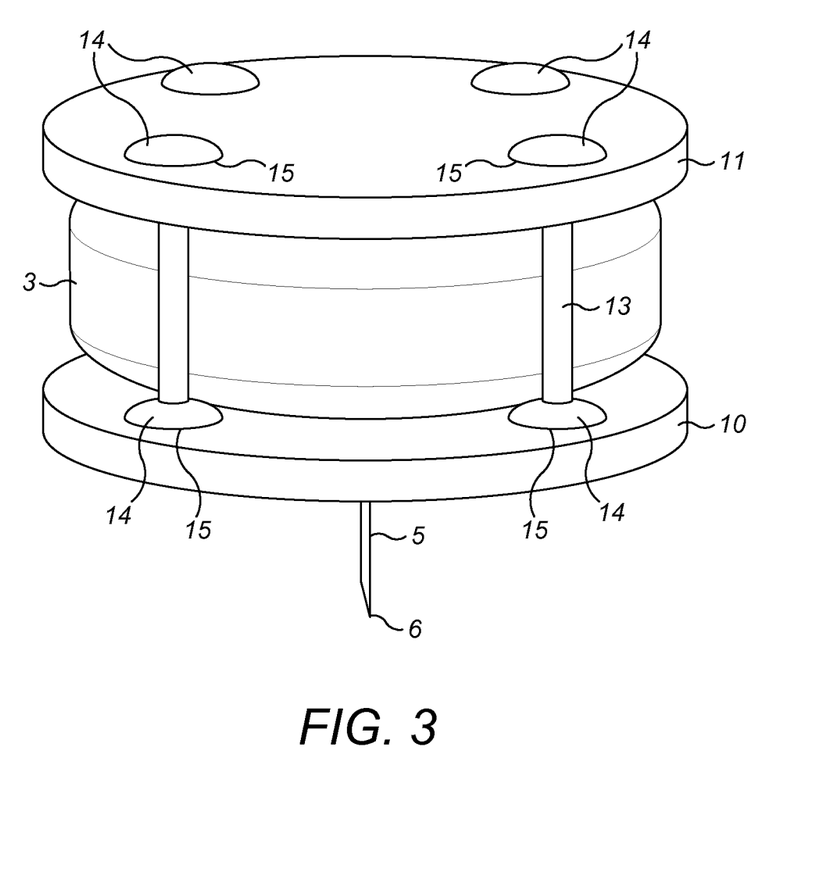
FIG. 3 shows a perspective view of the medicament delivery system of FIG. 1 in an expanded state, including a medicament container.
Figure 4A:
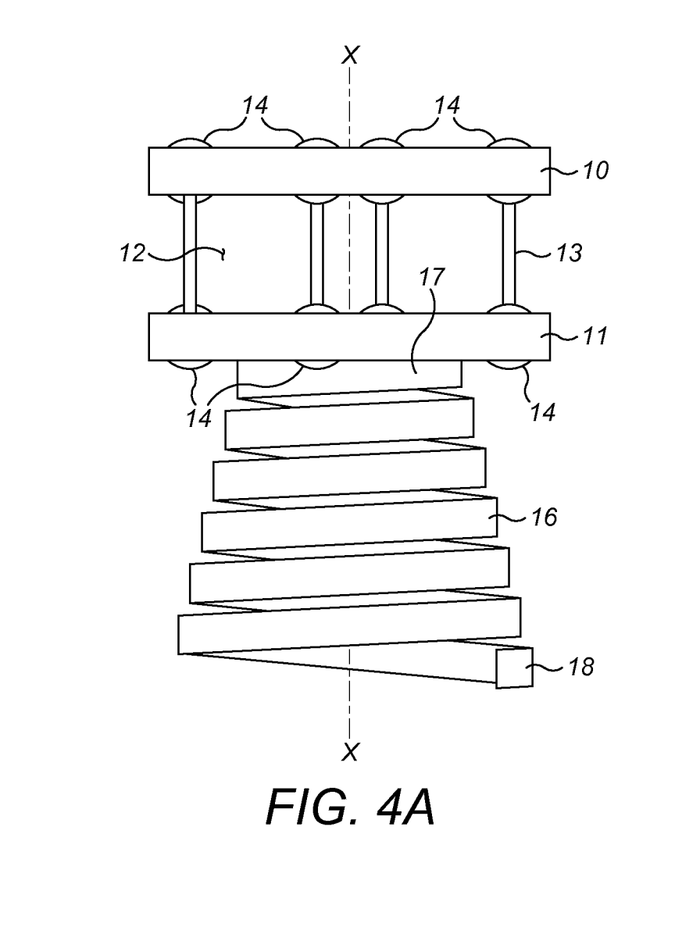
FIGS. 4A and 4B respectively show a side view and a perspective view of the medicament delivery system of FIG. 2 in an expanded state.
Figure 4B:
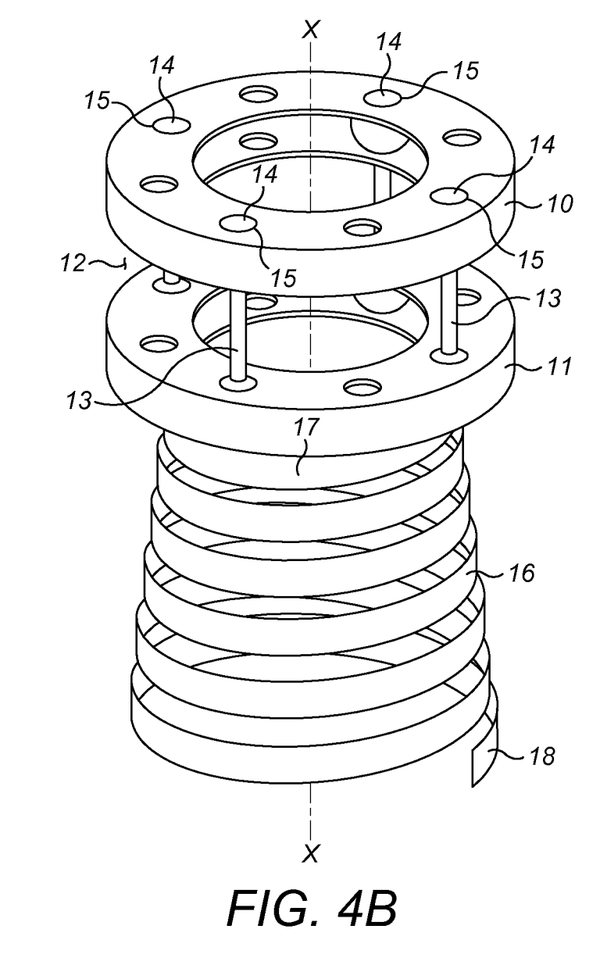

The medicament delivery system 2 is shown in more detail in various stages during use in FIGS. 4A to 6B. As with FIG. 2, FIGS. 4A to 6B show the medicament delivery system 2 without the medicament reservoir 3, for ease of illustration. FIGS. 4A and 4B show the medicament delivery system in a fully expanded state. That is, the support plate 10 and the compression plate 11 are spaced as far apart by the maximum distance permitted by the connecting rods 13. In such configuration, the connecting rods 13 extend substantially perpendicular to the support and compression plates 10, 11. Therefore, the respective spherical sockets 15 in the support and compression plates 10, 11 are aligned in the axial direction. In the fully expanded state, the gap 12 is therefore at its maximum size and accommodates the medicament reservoir 3 when full with medicament. This configuration is shown in FIG. 3, with the omission of the torsion spring 16.

Figure 5A:
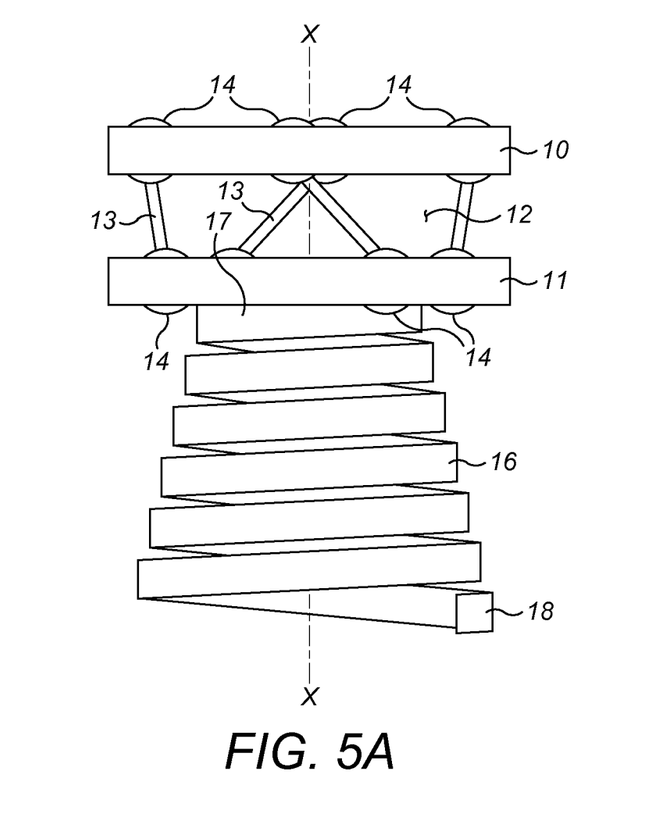
FIGS. 5A and 5B respectively show a side view and a perspective view of the medicament delivery system of FIG. 2 in a partially compressed state.
Figure 5B:
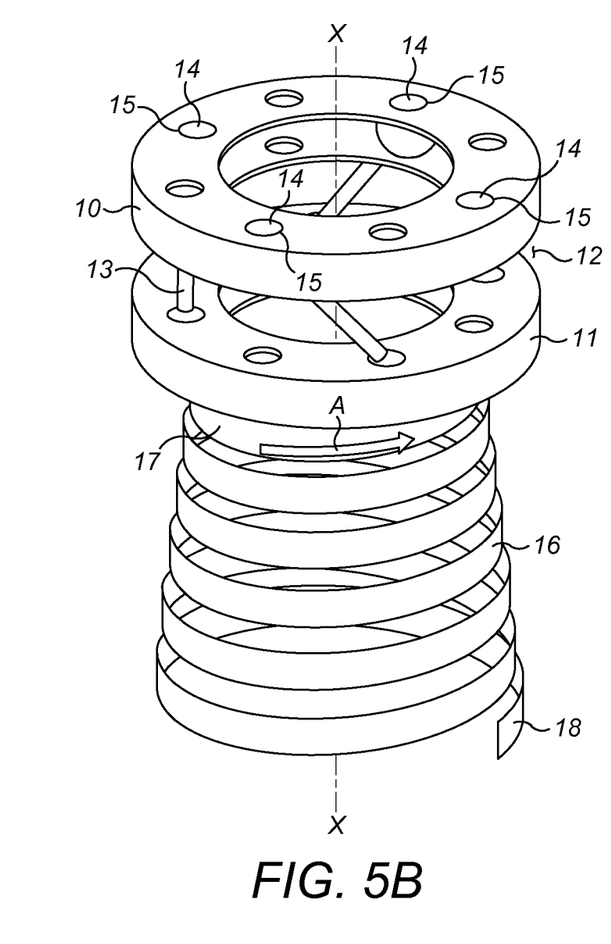

FIGS. 5A and 5B show the medicament delivery system 2 is a partially compressed state. Here the torsion spring 16 has been released by the locking mechanism 19 and urges the compression plate 11 in a rotational direction about axis X-X relative to the support plate 10. The compression plate 11 is thereby caused to rotate in the direction shown by arrow 'A' relative to the support plate 10. This causes the respective spherical sockets 15 in the support and compression plates 10, 11 to be rotationally off-set about the axis X-X. Since the connecting rods 13 are rigid and inextensible, this causes the compression plate 11 to be drawn towards the support plate 10, reducing the size of the gap 12. This causes the medicament reservoir 3 to be compressed and the medicament therein to be expelled from the medicament reservoir through the needle 5 into the patient.

Figure 6A:
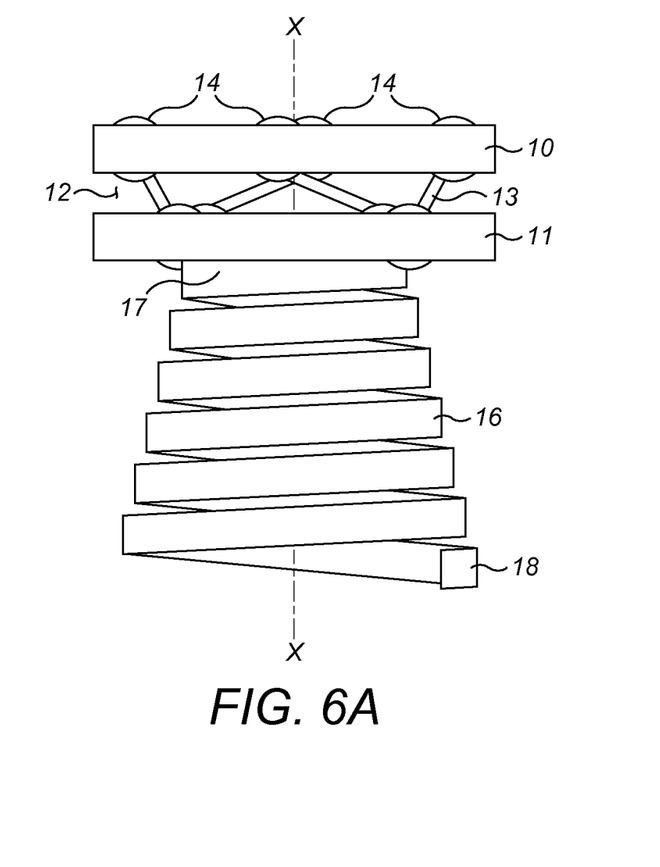
FIGS. 6A and 6B respectively show a side view and a perspective view of the medicament delivery system of FIG. 2 in a fully compressed state.
Figure 6B:
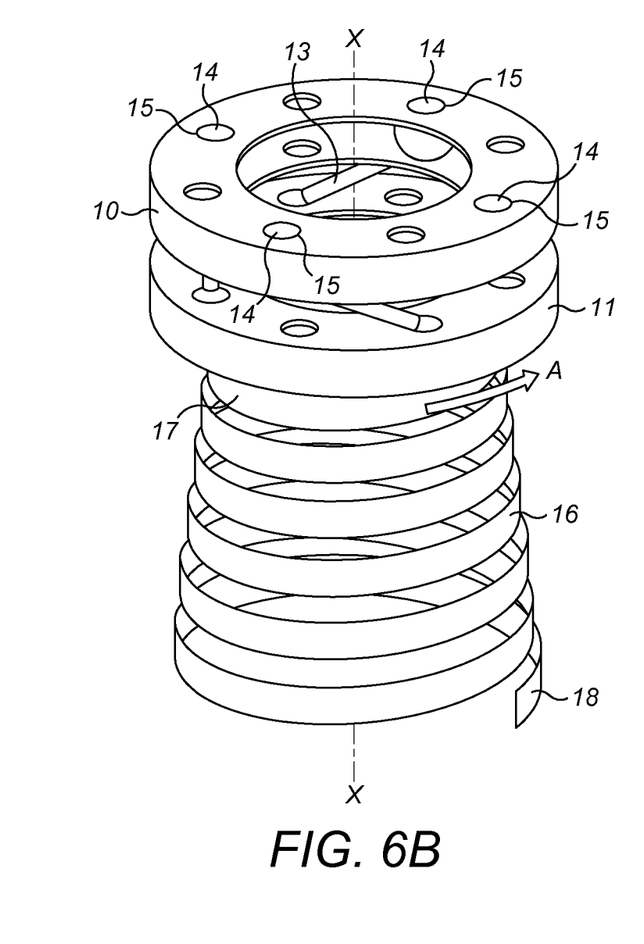

FIGS. 6A and 6B show the medicament delivery system 2 in a fully compressed state. Here, the torsion spring 16 has continued to urge the compression plate 11 in the direction of arrow 'A' in a rotational direction about axis X-X relative to the support plate 10. The compression plate 11 has been further drawn towards the support plate 10, further reducing the size of the gap 12. A medicament reservoir 3 disposed in the gap 12 would therefore have been further compressed and the full dose of the medicament therein would have been expelled from the medicament reservoir 3 through the needle 5 into the patient. As mentioned above, the torsion spring 16 may also be configured to exert a force on the compression plate 11 in an axial direction towards the support plate 10, as well as exerting a rotational force. This may beneficially further urge the medicament delivery system into the compressed state and so help compress the medicament reservoir 3 to expel the medicament therein.

Operation of the medicament injection device 1 will now be described. A user initially removes the protective covering from the adhesive layer 9 and applies the device 1 at the intended injection site, with the contact region 7 facing the patient's body. The distal end 6 of the needle 5 pierces the patient's skin. This may be by the control mechanism (not shown) moving the needle to an extended position, or by the placement of the device 1 at the injection site.

The release button 20 is pressed to disengage the locking mechanism 19. This releases the torsion spring 16 and/or compression plate 11. The torsion spring 16 urges the compression plate 11 in a rotational direction about axis X-X, as shown by arrow 'A' in FIGS. 5B and 6B. The compression plate 11 rotates relative to the support plate 10 about the axis X-X. However, since the connecting rods 13 are rigid and inextensible, the compression plate 11 is caused to also move towards the support plate 10 from the expanded state shown in FIGS. 4A and 4B to the partially compressed state shown in FIGS. 5A and 5B. The size of the gap 12 thereby reduces and so the flexible medicament reservoir 3 is squeezed between the support plate 10 and the compression plate 11. This causes the medicament within the medicament reservoir 3 to be expelled through the needle 5 into the patient's body.

The torsion spring 16 continues to rotationally urge the compression plate 11 and cause it to rotate relative to, and move towards, the support plate 10. This continues through the partially compressed state shown in FIGS. 5A and 5B until the device reaches the fully compressed state shown in FIGS. 6A and 6B. Once in the fully compressed state, the medicament reservoir 3 is collapsed to a point by which the full dose of medicament has been expelled though the needle 5 into the patient's body. The device 1 can then be removed from the patient's body and discarded or saved for reuse, if it is a reusable device that can be refilled/a replacement medicament reservoir installed.

FIG. 7 shows an alternative embodiment of a medicament injection device 1', including a medicament delivery system 2. Like features in common with the embodiment shown in FIG. 1 retain the same reference numerals and description thereof will not be repeated. The embodiment shown in FIG. 7 illustrates a control mechanism 21 configured to extend and retract the injection needle 5 and control a medicament injection process. The control mechanism 21 may comprise a control unit 22 to which the needle 5 is connected. The needle 5 may be connected to the control unit 22 via a valve 23 to enable control of the flow of medicament. A conduit 24 fluidly connects an outlet of the medicament reservoir 3 to the needle 5 via the control unit 22 and the valve 23.

The control unit 22 is mounted on a piston 25 to enable the needle 5 to move between a retracted position and an extended position, as shown by arrow 'B' in FIG. 7. In the retracted position, the needle is contained within the housing 4. In the extended position, the needle 5 extends through the hole 8 in the contact region 7. An injector spring 26 is provided to provide additional biasing force to assist the needle 5 moving to the extended position and piercing the patient's skin. An actuator 27 is provided on the housing 4 and is connected to the control unit 22. The actuator may comprise a button, switch or other suitable component. Pressing the actuator 27 causes the control unit 22 to move the injection needle 5 into the extended position ready for a medicament delivery process to be initiated by pressing the release button 20, as described previously. In an alternative embodiment however, the locking mechanism 19 may be connected to the control unit 22 (as shown by the dashed line in FIG. 7). In such an embodiment, the actuator 27 may be omitted. In such an embodiment, pressing the release button 20 would cause the control unit 22 to move the needle 5 into the extended position, and would also initiate medicament delivery by the medicament delivery system 2 as described previously. Flow of the medicament through the needle 5 may be controlled by the control unit 22 by opening the valve 23 once the needle 5 is fully inserted into the patient's body tissue. It will be appreciated that in such an embodiment, the needle injection step and the medicament delivery step would not be two independent steps to be performed by a user.

The control mechanism 21 may be electrically powered. For example, the piston 25 may be electrically powered. Electrical power may also be used to retract the injector spring 26, control unit 22 and injection needle 5 back to the retracted position, thereby withdrawing the injection needle 5. For this purpose, the control mechanism 21 may comprise an electrical motor (not shown) and a suitable drive mechanism (not shown) coupled to the piston 25. The electrical power may be provided by a battery (not shown) or other power source in the device 1, which may be rechargeable.

The control unit 22 may comprise an electronic controller (not shown) which is configured to control operation of various elements of the device 1. An alternative is for the control unit to operate under the control of a timing element, such as a mechanical timer. The timing element may be a count-down timer. The elapse of a count-down period of the timing element may indicate that an event has occurred, such as the completion of an injection of a dose of medicament. The elapse of the count-down period may cause the piston 25 to move the injection needle 5, for example by withdrawing the injection needle back into the housing 4 of the device 1.

Examples of alternative injection elements intended within the scope of certain aspects of the invention include a cannula which may be sharpened to facilitate its insertion into the body tissue of the patient. A separate needle (not shown) or trocar (not shown) may be provided for aiding the insertion of a distal end of such a cannula into the body tissue. The needle may be controllably extendable and/or retractable from the housing 4 of the device 1 in a similar manner to the hollow injection needle 5 discussed above. The needle may be configured to pierce the skin of the patient in order to allow the cannula to move into the body tissue. The needle may, for example, be arranged to extend through the centre of the cannula. Once the skin has been pierced, the device 1 may be configured to retract the needle back into the housing before delivery of the medicament. In the case that the device 1 comprises a separate needle of the type described above, the device may comprise an actuator to facilitate the extension and retraction of the needle.

It will be appreciated that the inventive concept of the medicament delivery system of certain aspects of the present invention may be applicable to LVDs. However, the invention is not intended to be limited to this particular type of medicament delivery device and certain aspects of the present invention are intended to cover alternative types of medicament delivery devices which include a medicament container to be received in a medicament delivery device which may include, but are not limited to, patch pumps and infusion pumps.

The terms "drug" or "medicament" which are used interchangeably herein, mean a pharmaceutical formulation that includes at least one pharmaceutically active compound. The term "drug delivery device" shall be understood to encompass any type of device, system or apparatus designed to immediately dispense a drug to a human or non-human body (veterinary applications are clearly contemplated by the present disclosure). By "immediately dispense" is meant an absence of any necessary intermediate manipulation of the drug by a user between discharge of the drug from the drug delivery device and administration to the human or non-human body. Without limitation, typical examples of drug delivery devices may be found in injection devices, inhalers, and stomach tube feeding systems. Again without limitation, exemplary injection devices may include, e.g., syringes, autoinjectors, injection pen devices and spinal injection systems.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis. Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine. Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in certain aspects of the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. A medicament delivery system for use with a medicament delivery device, the medicament delivery system comprising:
    a support member;
    a compression member spaced from the support member to define a gap between the compression member and the support member;
    a mechanical coupling between the support member and the compression member comprising a plurality of connecting members extending between the support member and the compression member; and
    a biasing element connected to the compression member and configured to exert a rotational force on the compression member relative to the support member,
    wherein the mechanical coupling is configured such that rotation of the compression member relative to the support member causes the compression member to be drawn towards the support member to reduce the gap between the compression member and the support member,
    wherein the mechanical coupling permits the compression member to rotate relative to the support member about an axis and permits the compression member to move towards the support member in a direction along the axis.

2. The medicament delivery system according to claim 1, wherein each of the plurality of connecting members is pivotally connected to the support member and to the compression member.

3. The medicament delivery system according to claim 2, wherein each of the plurality of connecting members is pivotally connected to the support member and the compression member by a ball and socket coupling.

4. The medicament delivery system according to claim 1, wherein the plurality of connecting members comprise inextensible rigid rods.

5. The medicament delivery system according to claim 1, wherein the biasing element is also configured to bias the compression member towards the support member.

6. The medicament delivery system according to claim 1, wherein the biasing element comprises a spiral torsion spring.

7. The medicament delivery system according to claim 6, wherein the spiral torsion spring is conically shaped.

8. The medicament delivery system according to claim 1, wherein the support member and the compression member comprise substantially parallel spaced plates.

9. The medicament delivery system according to claim 1, further comprising a collapsible medicament reservoir disposed in the gap between the support member and the compression member.

10. The medicament delivery system according to claim 9, wherein the compression member contacts a first side of the reservoir, and the support member contacts a second side of the reservoir, the first side being opposite the second side.

11. The medicament delivery system according to claim 1, wherein the compression member and the support member are coaxial along a longitudinal axis.

12. The medicament delivery system according to claim 1, wherein the mechanical coupling extends through the gap between the compression member and the support member.

13. The medicament delivery system according to claim 1, wherein:
    the compression member comprises a plurality of sockets,
    the support member comprises a plurality of sockets, and
    each of the plurality of connecting members comprises a first ball element retained within a corresponding one of the plurality of sockets of the compression member and a second ball element retained within a corresponding one of the plurality of sockets of the support member.

14. The medicament delivery system according to claim 1, wherein a planar surface of the compression member and a planar surface of the support member define the gap, the planar surfaces of the compression member and the support member being perpendicular to longitudinal axes along which the plurality of connecting members extend.

15. The medicament delivery system according to claim 1, wherein the mechanical coupling is configured to convert rotation of the compression member relative to the support member into movement of the compression member towards the support member.

16. The medicament delivery system according to claim 1, wherein the mechanical coupling is configured such that rotation of the compression member relative to the support member causes the compression member to be drawn towards the support member in a helical motion to reduce the gap between the compression member and the support member.

17. The medicament delivery system according to claim 1, wherein each connecting member of the plurality of connecting members extends from the support member to the compression member.

18. The medicament delivery system according to claim 1, wherein each connecting member of the plurality of connecting members is movable relative to the support member.

19. The medicament delivery system according to claim 1, wherein the compression member is rotatable about a longitudinal axis along which the plurality of connecting members extend relative to the support member.

20. The medicament delivery system according to claim 1, wherein the biasing element is coaxially coupled with the compression member.

21. A medicament delivery device comprising:
a housing;
a medicament delivery system disposed within the housing, the medicament delivery system comprising
a support member,
a compression member spaced from the support member to define a gap between the compression member and the support member,
a mechanical coupling between the support member and the compression member comprising a plurality of connecting members extending between the support member and the compression member, and
a biasing element connected to the compression member and configured to exert a rotational force on the compression member relative to the support member,
wherein the mechanical coupling is configured such that rotation of the compression member relative to the support member causes the compression member to be drawn towards the support member to reduce the gap between the compression member and the support member,
wherein the mechanical coupling permits the compression member to rotate relative to the support member about an axis and permits the compression member to move towards the support member in a direction along the axis;
a medicament reservoir; and
an injection needle fluidly connected to the medicament reservoir.

22. The medicament delivery device according to claim 21, comprising a releasable locking mechanism configured to retain the compression member against the rotational force of the biasing element.

23. The medicament delivery device according to claim 22, wherein the locking mechanism comprises an actuator operable to release compression member to move from an expanded state to a compressed state under the rotational force of the biasing element.

24. The medicament delivery device according to claim 21, further comprising a needle control mechanism configured to move the needle between a retracted position in which the needle is disposed within the housing and an extended position in which it projects from the housing.

25. The medicament delivery device according to claim 21, wherein the medicament reservoir contains liquid medicament.

26. A method of operating a medicament delivery system, the method comprising initiating an injection in which
a biasing element of the medicament delivery system exerts a rotational force on a compression member of the medicament delivery system relative to a support member of the medicament delivery system, wherein the compression member is spaced from the support member to define a gap between the compression member and the support member,
a mechanical coupling of the medicament delivery system converts rotation of the compression member relative to the support member to move the compression member towards the support member to reduce the gap between the compression member and the support member, wherein the mechanical coupling is between the support member and the compression member and comprises a plurality of connecting members extending between the support member and the compression member, and
a medicament reservoir of the medicament delivery system collapses to expel liquid medicament from the medicament reservoir,
wherein the mechanical coupling permits the compression member to rotate relative to the support member about an axis and permits the compression member to move towards the support member in a direction along the axis.

* * * * *